(12) United States Patent
Rizk

(10) Patent No.: US 9,018,150 B1
(45) Date of Patent: Apr. 28, 2015

(54) CLEANSING COMPOSITION WITH CATIONIC SURFACTANTS

(71) Applicant: L'Oreal, Paris (FR)

(72) Inventor: Kirolos Rizk, Helmetta, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/100,144

(22) Filed: Dec. 9, 2013

(51) Int. Cl.
| | |
|---|---|
| *C11D 1/02* | (2006.01) |
| *C11D 1/38* | (2006.01) |
| *C11D 1/83* | (2006.01) |
| *C11D 1/90* | (2006.01) |
| *C11D 1/94* | (2006.01) |
| *A61Q 5/02* | (2006.01) |
| *A61K 8/41* | (2006.01) |
| *A61K 8/42* | (2006.01) |
| *A61K 8/46* | (2006.01) |
| *A61K 8/60* | (2006.01) |
| *A61K 8/84* | (2006.01) |
| *A61Q 5/12* | (2006.01) |

(52) U.S. Cl.
CPC . *A61K 8/416* (2013.01); *A61K 8/42* (2013.01); *A61K 8/463* (2013.01); *A61K 8/466* (2013.01); *A61K 8/602* (2013.01); *A61K 8/84* (2013.01); *A61Q 5/02* (2013.01); *A61Q 5/12* (2013.01)

(58) Field of Classification Search
CPC ............ C11D 1/02; C11D 1/38; C11D 1/662; C11D 1/83; C11D 1/90; C11D 1/94; A61Q 5/02
USPC ......... 510/119, 121, 123, 125, 127, 426, 433, 510/474, 475, 504; 424/70.11, 70.19, 424/70.21, 70.24, 70.31
See application file for complete search history.

(56) References Cited

U.S. PATENT DOCUMENTS

| | | | |
|---|---|---|---|
| 6,110,451 A | 8/2000 | Matz et al. | |
| 6,489,286 B1 * | 12/2002 | Lukenbach et al. | ......... 510/475 |
| 2005/0071933 A1 | 4/2005 | Rondeau | |
| 2006/0135382 A1 | 6/2006 | Molenda | |
| 2006/0217283 A1 | 9/2006 | De Salvert et al. | |
| 2011/0139170 A1 * | 6/2011 | Hippe et al. | ................. 132/202 |
| 2011/0155163 A1 | 6/2011 | Viravau et al. | |
| 2011/0155164 A1 | 6/2011 | Viravau et al. | |
| 2012/0196783 A1 | 8/2012 | D'Aversa et al. | |
| 2012/0308492 A1 | 12/2012 | Allef et al. | |
| 2013/0143784 A1 | 6/2013 | Rizk | |

FOREIGN PATENT DOCUMENTS

| | | |
|---|---|---|
| EP | 1504749 B1 | 12/2008 |
| WO | 2010/069500 A1 | 6/2010 |

OTHER PUBLICATIONS

U.S. Appl. No. 14/100,117, filed Dec. 9, 2013, Kirolos Rizk.
U.S. Appl. No. 14/100,126, filed Dec. 9, 2013, Kirolos Rizk.
U.S. Appl. No. 14/100,144, filed Dec. 9, 2013, Kirolos Rizk.
U.S. Appl. No. 14/100,156, filed Dec. 9, 2013, Kirolos Rizk.
Jorg Kahre, Catherine Le Hen Ferrenbach, Laurence Robbe Tomine, Holger Tesmann, Tensio-Actifs Les alkylpolyglucosides une nouveaute en matiere de soin et de tolerance, Parfums Cosmetiques Actualites No. 131, Nov. 1996, pp. 49-61.

* cited by examiner

*Primary Examiner* — Brian P Mruk
(74) *Attorney, Agent, or Firm* — Novak Druce Connolly Bove + Quigg LLP

(57) ABSTRACT

Disclosed is a cleansing composition containing from about 6% to about 20% of at least one nonionic surfactant; from about 3% to about 10% of at least one amphoteric surfactant; from about 2% to about 8% of at least one anionic surfactant; and from about 0.1% to about 5% of at least one cationic conditioning surfactant, cationic conditioning amine, or a mixture thereof; wherein the amount of nonionic surfactant present in the final composition is greater than the amount of the amphoteric surfactant, and the ratio of the nonionic surfactant (a) to anionic surfactant (c) is at least about 1.9 as much as the anionic surfactant, based on the weight percent of each surfactant in the final composition.

22 Claims, No Drawings

CLEANSING COMPOSITION WITH CATIONIC SURFACTANTS

TECHNICAL FIELD

The present invention relates to personal cleansing compositions. More particularly, the invention relates to a shampoo composition having not only exceptional cleaning effect, but also improved conditioning properties.

BACKGROUND OF THE INVENTION

Conventional cleansing compositions such as shampoos, for example, contain standard surfactants such as anionic, nonionic and/or amphoteric type surfactants in amounts such that the anionic surfactant is typical present in the highest concentration of the foregoing three surfactants. This is because these anionic surfactants provide optimal foaming to the final composition. While nonionic surfactants are also often used in the cosmetic industry as they offer good cleansing, solubilizing and dispersing properties and are less irritating than anionic surfactants, their usage is typically limited to the secondary surfactant by percent in comparison to anionic surfactants due to their poor foaming ability as well as providing lower viscosity to the overall composition (i.e. the composition is thinner and more runny with increased amounts of the nonionic surfactant).

These cleaning compositions can be applied onto a wet keratinous substrate (e.g. hair or skin) and the lather they generate make it possible, after rinsing with water, to remove the diverse types of soils typically present on the hair or skin.

While these compositions provide good cleansing power, they often have poor intrinsic cosmetic properties due to the fact that the relatively aggressive nature of such a cleansing treatment may, in the long term, give rise to more or less pronounced damage on hair fibers or skin associated, for example, with the gradual removal of the fats or proteins contained in or at their surface.

Thus, in order to improve the cosmetic properties of cleansing compositions, it is now common practice to introduce into these compositions certain cationic conditioning ingredients such as polymers and silicones for use as conditioning agents in order to improve the tactile properties of said compositions. Cationic surfactants are known to act as conditioning agents and detangling aids in hair conditioner and hair treatment formulations. These typical conditioner/detangling formulations are primarily comprised of water and do not typically contain anionic cleansing surfactants. While it is in theory desirable, it is very unusual to include the above-mentioned cationic surfactants or conditioning amines in shampoo compositions as the strong interaction and affinity of cationic ingredients with anionic cleansing surfactants can, and most often does lead to the formation of insoluble salts which causes phase separation resulting in unstable formulations.

It is an object of the present invention to provide high foaming, effective cleaning compositions for use in personal care that also can provide increased conditioning effects, are stable and cost-effective.

BRIEF SUMMARY OF THE INVENTION

The present invention relates to an aqueous cleansing composition comprising:
(a) from about 6% to about 20% of at least one nonionic surfactant;
(b) from about 3% to about 10% of at least one amphoteric surfactant;
(c) from about 2% to about 8% of at least one anionic surfactant; and
(d) from about 0.1% to about 5% of at least one cationic conditioning surfactant, cationic conditioning amine, or a mixture thereof;
wherein the amount of nonionic surfactant (a) present in the final composition is greater than the amount of the amphoteric surfactant (b), and the ratio of nonionic surfactant (a) to anionic surfactant (c) is at least about 1.9:1, by weight, based on the weight percent of each surfactant in the final composition.

The present invention is also directed to a process for cleansing and conditioning a keratinous substrate involving contacting the keratinous substrate with the above-disclosed composition.

The present invention is also directed to a method of conditioning a keratinous substrate involving contacting the keratinous substrate with the above-disclosed composition.

The present invention is also directed to a method of increasing the deposition of hydrophobic non-ionic conditioning agents (such as silicones and oils) onto a keratinous substrate involving contacting the keratinous substrate with a non-ionic conditioning agent and the composition of the invention.

The present aqueous composition results from the finding that a blend of a specific amount and ratio of cleansing surfactants enables the composition additionally to incorporate at least one cationic conditioning surfactant and/or cationic conditioning amine, the latter compounds not typically found in traditional shampoo compositions. The present composition provides not only good cleansing of keratinous substrates, but also affords foam having good volume and luxurious feel, while at the same time imparting increased conditioning properties onto the substrate all while reducing the amount of anionic surfactant. The composition is clear in appearance and highly viscous.

It is to be understood that both the foregoing general description and the following detailed description are exemplary and explanatory only, and are not restrictive of the invention.

DETAILED DESCRIPTION OF THE INVENTION

The present compositions provide not only good cleansing of keratinous substrates, but also create good and luxuriously feeling foam, while at the same time imparting increased conditioning properties onto the substrate all while reducing the amount of anionic surfactant. When used as shampoos, these compositions have foaming qualities at least comparable to, most often better than, traditional shampoos, even though they use nonionic surfactants as the primary surfactants and anionic surfactants only as tertiary surfactants. Also, because the compositions use an nonionic surfactant as the primary surfactant, the compositions have lower irritation potential as compared to traditional anionic-rich cleaning compositions.

Moreover and quite unexpectedly, these compositions are stable even with high concentrations of cationic conditioning surfactants and/or cationic conditioning amines. These compositions thus afford increased delivery of cationic conditioning agents in comparison to traditional anionic-based cleaning compositions. When used as shampoos, these compositions deliver conditioner to the hair in a manner in which the conditioner clings to and stays on the hair even after repeated washings. This is believed to be due to the higher quantity of nonionic surfactant in the composition which allows for better compatibility with the above cationic agent(s) and improves overall stability in contrast to classical shampoos. This is true even with cationic conditioning surfactants (e.g., cetrimonium chloride ("CATC")) or cationic conditioning amines (e.g. stearamidopropyl dimethyl amine). These classes of charged conditioning agents have typically not been incorporated in traditional shampoo compositions due in part to the strong charge attraction and high degree of complexing between the cationic conditioning agents and anionic cleansing surfactants which can lead to formation of insoluble salts resulting in unstable compositions. Thus, the low degree of complexing in the current compositions allows for the incorporation of these cationic agents in the present shampoo compositions even though these cationic agents are not typically used in traditional shampoo compositions. Moreover and unexpectedly, the compositions of the invention remain stable at room temperature for several months in contrast to classical anion-rich shampoos which typically separate within hours. The low degree of complexing also allows for greater deposition of the cationic conditioning surfactants and/or cationic conditioning amines onto anionically charged hair fibers. These compositions thus provide for greater conditioning effect than traditional shampoos thereby minimizing the need for additional conditioning agents such as silicones, yielding overall cost savings.

All percentages and ratios are calculated by weight unless otherwise indicated. All percentages are calculated based on the total composition unless otherwise indicated.

As used herein, all ranges provided are meant to include every specific range within, and combination of sub ranges between, the give ranges. Thus, a range from 1 to 5, includes specifically 1, 2, 3, 4 and 5, as well as 2-5, 3-5, 2-3, 2-4, 1-4, etc.

"A" and "the" as used herein are understood to encompass the plural as well as the singular.

"About" as used herein means within 10% of the indicated number (e.g. "about 10%" means 9%-11% and "about 2%" means 1.8%-2.2%).

"At least one" as used herein means one or more and thus includes individual components as well as mixtures/combinations.

"Clear" as used herein means that the composition is visually clear (a person is able to see through the composition with their naked eyes). It also means that the composition does not exhibit phase separation. The clarity of a formulation can be measured by the transmittance percentage of light with a wavelength of 700 nm by UV-Visible spectrophotometry. "Clear" samples allow for about 60% or higher, more preferably about 70% or higher, even more preferably about 80% or higher, of the light to pass through the formula.

"Comprising" as used herein is used in the inclusive sense of "having" or "including" and not in the exclusive sense of "consisting only of."

"Conditioning" as used herein means imparting to hair at least one property chosen from compatibility, manageability, moisture-retentivity, luster, shine, and softness. The state of conditioning is evaluated by measuring, and comparing the ease of combing of the treated hair in contrast with the untreated hair.

"Good foam" means that the foam produced is in high quantity and is stable and creamy over the period of use.

"HLB" as used herein means the hydrophilic-lipophilic balance of a molecule. It is the ratio between the hydrophilic part and lipophilic part of a molecule. This term is well known to those skilled in the art. See, e.g., "The HLB System: A Time-saving Guide to Emulsifier Selection" (Pub: ICI Americas Inc., 1984) and US2006/0217283 at [0053], both of which are herein incorporated by reference.

"Keratinous substrates", as used herein, include but are not limited to, skin, hair, lips, eyelashes and nails. A Preferred keratinous substrate is hair.

In an embodiment, the invention relates to an aqueous cleansing composition comprising:
(a) from about 6% to about 20% of at least one nonionic surfactant;
(b) from about 3% to about 10% of at least one amphoteric surfactant;
(c) from about 2% to about 8% of at least one anionic surfactant; and
(d) from about 0.1% to about 5% of at least one cationic conditioning surfactant or cationic conditioning amine, or a mixture thereof;
  wherein the amount of nonionic surfactant (a) present in the final composition is greater than the amount of the amphoteric surfactant (b), and the ratio of nonionic surfactant (a) to anionic surfactant (c) is at least about 1.9:1, by weight, based on the weight percent of each surfactant in the final composition.

In a preferred embodiment the amount of nonionic surfactant (a) is at least 2 times as much as the amount of anionic surfactant (c). In another embodiment, the amount of nonionic surfactant (a) is about 2.3 times as much as the amount of anionic surfactant (c). In another embodiment, the amount of non-ionic surfactant (a) is about 2.5 times as much as the amount anionic surfactant (c).

Nonionic Surfactants (Component (a))

Non-ionic surfactants, while they are known for good cleaning properties, are not preferred in commercial shampoos in part as they are typically too harsh and drying on keratinous substrates (e.g. hair). However, the ratio of this surfactant to and its association with the amphoteric surfactant of the invention enables the use of non-ionic surfactants in the current cleansing formulation and still yield a conditioning effect.

The at least one nonionic surfactant useful in the cosmetic compositions disclosed herein is selected from: alkyl polyglucosides; ethylene glycol, propylene glycol, glycerol, polyglyceryl esters and their ethoxylated derivatives (herein jointly referred to as "glycol esters"); as well as amine oxides; and mixtures the foregoing.

Alkyl polyglucosides useful in the compositions of the invention include those having the following formula (I):

$$R^1-O-(R^2O)n-Z(x) \tag{I}$$

wherein
  $R^1$ is an alkyl group having 8-18 carbon atoms;
  $R^2$ is an ethylene or propylene group;
  Z is a saccharide group with 5 to 6 carbon atoms;
  n is an integer from 0 to 10; and
  x is an integer from 1 to 5.

Such alkyl poly glucoside compounds include lauryl glucoside, octyl glucoside, decyl glucoside, coco glucoside, sucrose laurate, caprylyl/capryl glucoside, and sodium lauryl glucose carboxylate, and mixtures thereof. Typically, the at least one alkyl poly glucoside compound is selected from the group consisting of lauryl glucoside, decyl glucoside and coco glucoside, and more typically lauryl glucoside.

Non-limiting examples of glycol esters useful in the compositions of the invention include those described in M. R. Porter et al., Handbook of Surfactants, Ch. 7, §7.12, pp. 231-235 ($2^{nd}$ Ed. 1994), herein incorporated by reference. Preferred glycol esters have HLB values between about 9 and about 18. Particular glycol esters useful in the compositions of the invention include PEG-8 glyceryl laurate, polysorbate-40, polyglyceryl-5 laurate, and mixtures thereof.

Amine oxides useful in the compositions of the invention include those having the formulas (IIA) and (IIB)

(IIA), and

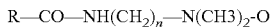

(IIB)

wherein
R is an alkyl group having 8-18 carbon atoms; and
n is an integer from 1 to 3.

A non-limiting example of a particular amine oxide is lauramine oxide.

In the present compositions, the at least one nonionic surfactant is used in an amount of from about 6% to about 20%, typically from about 7% to about 10%, and more typically about 7.15%, including all ranges and sub ranges therebetween, by weight based on the total weight of the composition as a whole.

Amphoteric Surfactant (Component (b))

The at least one amphoteric surfactant useful in the cosmetic compositions disclosed herein is chosen from betaines, sultaines, amphoacetates, amphoprorionates, and mixtures thereof. More typically, betaines and amphoprorionates are used, and most typically betaines. Betaines which can be used in the current compositions include those having the formulas (III A-D) below:

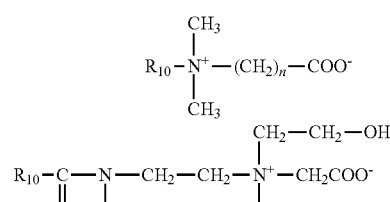

(III A-B)

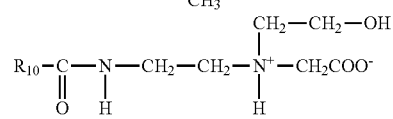

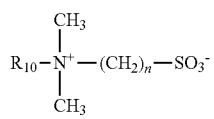

(III C)

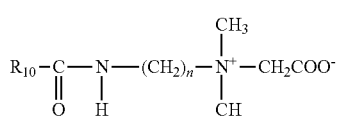

(III D)

wherein
$R^{10}$ is an alkyl group having 8-18 carbon atoms; and
n is an integer from 1 to 3.

Particularly useful betaines include, for example, coco betaine, cocoamidopropyl betaine, lauryl betaine, laurylihydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/caprami-dopropyl betaine, and lauryl betaine, and mixtures thereof, and more typically cocoamidopropyl betaine.

Hydroxyl sultaines useful in the compositions of the invention include the following

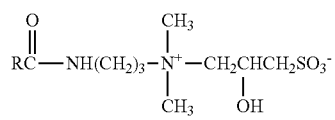

(IV)

wherein
R is an alkyl group having 8-18 carbon atoms.

Useful alkylamphoacetates include those having the formula (V)

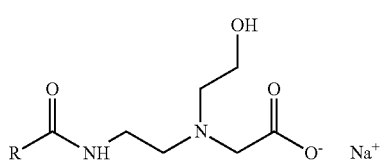

(V)

wherein
R is an alkyl group having 8-18 carbon atoms.

Useful alkylamphodiacetates include those having the formula (VI)

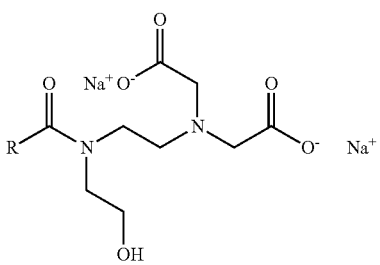

(VI)

wherein
R is an alkyl group having 8-18 carbon atoms.

In the present compositions, the at least one amphoteric surfactant is used in an amount of from about 3% to about 10% by weight, typically from about 4% to about 8% by weight, and more typically about 5.7% by weight, including all ranges and sub ranges therebetween, based on the total weight of the composition as a whole.

Anionic Surfactant (Component (c))

The at least one anionic surfactant used in the cosmetic compositions disclosed herein can be, for example, chosen from salts, for example, alkali metal salts such as sodium salts, ammonium salts, amine salts, amino alcohol salts and alkaline-earth metal salts, for example magnesium salts, of the following types of compounds: alkyl sulfates, alkyl ether sulfates, acyl isethionates, acyl glycianates, acyl taurates, acyl amino acids, acyl sarcosinates, sulfosuccinates, sulfonates, fulfoacetates, the alkyl and acyl groups of all these compounds comprising from 6 to 24 carbon atoms (saturated or unsaturated, linear or branched).

Particular sulfate salts useful in the invention include those having the formulas (VII A and B)

Isethionate:

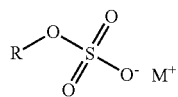

and

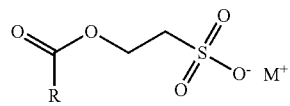

wherein

R is alkyl chain having 6 to 24 carbon atoms;
M is an alkali-metal salt as described above; and
n is an integer from 0 to 3.

Particular sulfate salts useful in the invention include those having the formulas (VII A and B)

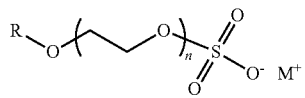

and

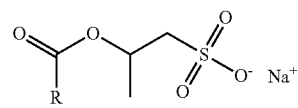

Sulfosuccinates:

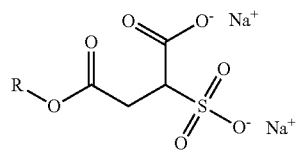

Sulfonates:

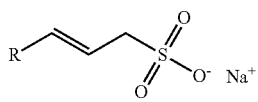

wherein in the above formulas R, $R^1$, $R^2$ and $R^3$ are each independently selected from H or alkyl chain that has 1-24 carbon atoms, said chain being saturated or unsaturated, linear or branched, and X is COO— or $SO_3$—.

Non-limiting examples of alkyl ether sulfates that can be used in the current compositions include lauryl sulfate, laureth sulfate, and salts and mixtures of these. More particularly, the lauryl sulfate is sodium lauryl sulfate and the laureth sulfate is sodium laureth sulfate.

Non-limiting examples of isethionates that can be used in the current compositions include sodium cocoyl isethionate, sodium lauroyl methyl isethionate, and mixtures thereof.

A non-limiting example of a taurate that can be used in the current compositions is sodium methyl cocoyl taurate.

Acyl amino acids that can be used in the current compositions include amino acid surfactants based on glycine, sarcosine, threonine, glutamine, glutamic acid or alanine. The most common salt ion attached to the at least one acyl amino acid can be sodium or potassium. The salt ion attached to the acyl amino group can also be an organic salt, such as triethanolamine (TEA), or a metal salt. Examples of acyl amino acid compounds include but are not limited to: sodium cocoyl glycinate, potassium cocoyl glycinate, and sodium lauryl sarcosinate, sodium cocoyl alaninate, and salts thereof. Typically, the at least one acyl amino acid is selected from the group consisting of sodium cocoyl glycinate and potassium cocoyl glycinate, and in particular sodium cocoyl glycinate.

Non-limiting examples of sulfosuccinates that can be used in the current compositions are disodium laurel sulfosuccinate, sodium laureth sulfoscuccinate, and mixtures thereof.

Non-limiting examples of acyl amino acids, taurates, isethionate, sulfosuccinates and sulfonates useful in the compositions of the invention include those having the following formulas:

Acyl amino acids:

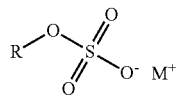

Taurates:

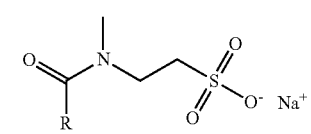

A non-limiting example of a sulfonate that can be used in the current compositions is sodium C14-16 olefin sulfonate.

A non-limiting example of a sulfoacetate that can be used in the current compositions is sodium lauryl sulfoacetate.

In an embodiment, the anionic surfactant is selected from sodium cocoyl glycinate, sodium laureth sulfate, sodium laureth sulfoscuccinate, sodium lauryl sulfoacetate, and mixtures thereof.

The at least one anionic surfactant is present in a total amount ranging from about 2% to about 8% by weight, typically from about 2.5% to about 5%, more typically about 3% by weight, including all ranges and sub ranges therebetween, based on the total weight of the composition as a whole.

Cationic Conditioning Surfactant and Cationic Conditioning Amines (Component (d))

The cationic conditioning surfactant useful in the cosmetic compositions disclosed herein optionally is selected from mono and di-alkyl quaternary ammonium or diammonium salts.

By way of example only, quaternary ammonium or diammonium salts described in US2005071933, incorporated by reference herein, may be chosen, such as, for example, those of the general formula (XXI):

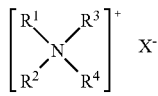

wherein, in formula (XXI):

—R1 and R4, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among R1, R2, R3 and R4 denoting a radical comprising from 8 to 30 carbon atoms; and —X⁻ is an anion chosen from the group comprising halides, phosphates, acetates, lactates and alkyl sulfates;

and/or general formula (XXII):

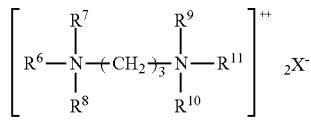

wherein, in formula (XXII):

—R6 denotes an aliphatic radical comprising from about 16 to 30 carbon atoms,

—R7, R8, R9, R10 and R11 are independently chosen from hydrogen or an alkyl radical comprising from 1 to 4 carbon atoms, and —X⁻ is an anion chosen from the group comprising halides, acetates, phosphates and sulfates Quaternary ammonium and diammonium salts include, for example, distearyldimethylammonium chloride, cetyltrimethylammonium chloride, behenyltrimethylammonium chloride, behentrimonium chloride, cetrimonium chloride oleocetyldimethylhydroxyethylammonium chloride, stearamidopropyldimethyl (myristyl acetate) ammonium chloride, di($C_1$-$C_2$ alkyl) ($C_{12}$-$C_{22}$ alkyl)hydroxy($C_1$-$C_2$alkyl) ammonium salt, such as dialkyldimethylammonium or alkyltrimethylammonium salt in which the alkyl radical preferably comprises 12 to 24 carbon atoms, propanetallowediammonium dichloride, behentrimonium methosulfate, and mixtures thereof.

Non-limiting examples of particular quaternary ammonium salts that can be used in the current compositions include in particular behentrimonium chloride, cetrimonium chloride, behentrimonium methosulfate, and mixtures thereof.

Non-limiting examples of cationic conditioning amines that can be used in the current compositions include dimethylamine derivatives, such as for example stearyl dimethyl amine, stearamidopropopy dimethyliamine, brassicamidopropyl dimethylamine, and mixtures thereof.

In an embodiment the cationic conditioning agent (d) is selected from stearamidipropyli dimethylamine, cetrimonium chloride, behentrimonium chloride, and mixtures thereof.

The at least one cationic conditioning surfactant and/or amine is present in the compositions of the invention in an amount of from about 0.1% to about 5% by weight, typically from about 0.5% to about 3% by weight, and more typically from about 0.75% to about 2%, by weight, including all ranges and sub ranges therebetween, based on the total weight of the composition as a whole. In a particular embodiment, the amount of cationic conditioning surfactant and/or amine is present at about 1% by weight, based on the total weight of the composition as a whole.

Additives

The composition of the present disclosure may additionally include any other adjuvant or additive that is usually used in the field of self-cleaning products, in particular shampoos. A person skilled in the art would know which adjuvants and/or additives to select to achieve the desired results (e.g. preservatives) without adversely affecting the properties of claimed emulsions. For example, such additives include pH adjusting agents, preserving agents, sequestrants and chelators, consistency regulators (e.g. isopropyl alcohol), thickeners, pH-regulators, antioxidants, fragrances, dyestuffs such as soluble dyes and pigments, optical brighteners, electrolytes and stabilizers (e.g. sodium chloride, glycerin), plant extracts, proteins, amino acids, vitamins, glycols, emollients, derivatives of the foregoing, and mixtures thereof. Such additives are described, for example in US2012/0308492 at [0079]-[0080] and US2006/0217283 at [0084]-[0087] both of which are herein incorporated by reference. These additives may be hydrophobic or hydrophilic.

Non-limiting examples of pH adjusting agents includes potassium acetate, potassium hydroxide, sodium carbonate, sodium hydroxide, phosphoric acid, succinic acid, sodium citrate, citric acid, boric acid, lactic acid, sodium hydrogen carbonate, ethanol amines, and mixtures thereof. In a particular embodiment, the pH adjusting agent is selected from potassium hydroxide, sodium hydroxide, ethanol amines, and mixtures thereof. In a particular embodiment, the pH adjusting agent is selected from sodium hydroxide, potassium hydroxide and ethanol amines, and mixtures thereof.

Non-limiting examples of useful preservatives include ethanol, polyvinyl alcohol, phenoxyethanol, benzyl alcohol, salicylic acid, sodium benzoate, benzoic acid, caprylyl glycol, methyl paraben, propyl paraben, ethylhexylglycerin, 1,3-propanediol, cholorphensin, methylchloroisothiazolinone, methylisothiazolinone, benzalkonium chloride, polyaminopropyl biguanide, and mixtures thereof. In a particular embodiment, the pH adjusting agent is selected from cholorphensin, methylchloroisothiazolinone, methylisothiazolinone, benzalkonium chloride, polyaminopropyl biguanide, and mixtures thereof.

Chelating agents and antioxidants are ingredients which assist in preventing or retarding spoilage. Examples of antioxidants suitable for use in the present composition are potassium sulfite, sodium bisulfite, sodium erythrobate, sodium metabisulfite, sodium sulfite, propyl gallate, cysteine hydrochloride, butylated hydroxytoluene, butylated hydroxyanisole, and mixtures thereof. Suitable chelators include salts of ethylenediaminetetraacetic acid ("EDTA"), tetrasodium EDTA, butylated hydroxytoluene ("BHT"), and mixtures thereof.

The cleansing compositions of the present invention have a pH of from about 3 to about 9, more typically between about 4 and about 8, in particular between about 5 and 7, including all ranges and sub ranges therein. Additionally, the cleansing compositions are preferably clear.

The present cleansing composition has a viscosity of about 2500 cPs to about 30000 cPs, typically from about 3000 cPs to about 20,000 cPs, particularly from about 3000 cPs to about 6000 cPs, more likely between about 4000 cPs and about 6000 cPs, including all ranges and sub ranges therebetween, measured using Brookfield viscometer as discussed below in the examples.

In an embodiment, the present invention relates to an aqueous cleaning and conditioning composition comprising:
(a) from about 6% to about 20% of at least one nonionic surfactant selected from alkyl polyglucosides and glycol esters, and mixtures thereof;
(b) from about 3% to about 10% of at least one amphoteric surfactant selected from betaines, sultaines, amphoacetates and amphoprionates, and mixtures thereof;
(c) from about 2% to about 8% of at least one anionic surfactant selected from lauryl sulfates, laureth sulfates, isethionates, glutamates, alaninates, glycinates, taurates, acyl amino acids, sarcosinates, sulfosuccinates, sulfonates, alkyl polyglucoside sulfonates and alkyl polyglucoside carboxylates, and mixtures thereof; and
(d) from about 0.1% to about 5% of at least one mono or di-alkyl quaternary ammonium salt wherein the alkyl group contains 6-24 carbon atoms and may be saturated or unsaturated;
wherein the amount of nonionic surfactant (a) present in the final composition is greater than the amount of the amphoteric surfactant (b), and the ratio of nonionic surfactant (a) to anionic surfactant (c) is at least about 1.9:1, by weight, based on the weight percent of each surfactant in the final composition.

In an embodiment, the ratio of the amount of nonionic surfactant (a) present in the final composition to the amount of anionic surfactant (c) is from about 1.9:1 to about 16:1, more typically from about 2:1 to about 10:1, particularly from about 2:1 to about 5:1, and more particularly about 2:1, including all ratios and ranges therebetween.

In a particular embodiment, the present invention relates to an aqueous cleaning and conditioning composition comprising:
(a) from about 6% to about 20% of at least one nonionic surfactant selected from lauryl glucoside, decyl glucoside, and mixtures thereof;
(b) from about 3% to about 10% of at least one amphoteric surfactant selected from cocoamphopropionate, cocoamidopropyl betaine, and mixtures thereof;
(c) from about 2% to about 8% of at least one anionic surfactant selected from sodium cocoyl taurate, sodium cocoyl glycinate, sodium cocoyl taurate, and sodium laureth sulfate, and mixtures thereof; and
(d) from about 0.1% to about 5% of at least one cationic conditioning surfactant or cationic conditioning amine selected from behentrimonium chloride, cetrimonium chloride, behentrimonium methosulfate, stearyl dimethyl amine, stearamidopropyl dimethylamine, and mixtures thereof;
wherein the amount of nonionic surfactant (a) present in the final composition is greater than the amount of the amphoteric surfactant (b), and the ratio of nonionic surfactant (a) to anionic surfactant (c) is from about 2:1 to about 5:1, including all ratios and ranges therebetween, based on the weight percent of each surfactant in the final composition.

The present invention is also directed to a process for cleansing and conditioning a keratinous substrate involving contacting the keratinous substrate with the above-disclosed cleansing composition. Preferably the keratinous substrate is hair.

It has also been found that the current formulation also increases/improves the deposition of hydrophobic non-ionic conditioning agents, for example silicones and oils, onto a keratinous substrate. Thus, in another embodiment, the invention is also directed to a method of increasing the deposition of hydrophobic non-ionic conditioning agents onto a keratinous substrate comprising contacting the keratinous substrate with a non-ionic conditioning agent and a composition of the invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis unless otherwise specified.

EXAMPLES

Preparation:
The compositions of the examples below were prepared by adding the nonionic, amphoteric and anionic surfactants to water and mixing while hearing to 50° C. until the mixture was uniform. To the extent used, fragrances, preservatives and conditioning agent (s) were then added. All of the compositions in the examples were clear gel-like compositions. Depending on the surfactants used, the compositions were colorless, yellow or brownish. Clarity of the compositions was measured by the transmittance percentage of light with a wavelength of 700 nm by UV-visible spectrophotometry.

Table 1: Examples 1-5 Compositions Having Various Surfactant Substitutions

TABLE 1

Examples 1-5 Compositions Having Various Surfactant Substitutions

| Ingredient category | INCI Name | Ex 1 | Ex 2 | Ex 3 | Ex 4 | Ex 5 |
| --- | --- | --- | --- | --- | --- | --- |
| Water, Preservatives, Dyes, Fragrance | | QS | QS | QS | QS | QS |
| Nonionic surfactant (a) | LAURYL GLUCOSIDE | 7.15 | 7.15 | 7.15 | 7.15 | 7.15 |
| Amphoteric surfactant (b) | COCAMIDOPROPYL BETAINE | 5.7 | 5.7 | 5.7 | 5.7 | 5.7 |
| Anionic Surfactant (c) | SODIUM COCOYL GLYCINATE | | | 3 | 3 | 3 |
| Anionic Surfactant (c) | SODIUM LAURETH SULFATE | 3 | | | | |

TABLE 1-continued

Examples 1-5 Compositions Having Various Surfactant Substitutions

| Ingredient category | INCI Name | Ex 1 | Ex | Ex 3 | Ex 4 | Ex 5 |
|---|---|---|---|---|---|---|
| Anionic Surfactant (c) | SODIUM LAURETH SULFOSUCCINATE (and) SODIUM LAURYL SULFOACETATE | | 3 | | | |
| Cationic Conditioning agent (d) | STEARAMIDIPROPYL DIMETHYLAMINE | | | | 1 | |
| Cationic Conditioning agent (d) | CETRIMONIUM CHLORIDE | 1 | 1 | 1 | | |
| Cationic Conditioning agent (d) | BEHENTRIMONIUM CHLORIDE | | | | | 1 |

As is shown above in Examples 1-5, the compositions of the invention can accommodate higher amounts (e.g. 1% or higher) of charged cationic surfactants and amines that are not typically found in currently available commercial shampoo formulations and still remain stable.

Evaluation Protocols

Stability:

The composition of Example 1 was stored at reduced temperatures (4-6° C.), elevated temperatures (37-50° C.), and room temperature for at least 8 weeks. Properties evaluated included visual inspection (phase separation), stability of pH, and stability of acceptable usage viscosity 2000-40,000 cps measured using a Brookfield viscometer. A product was considered stable if it passed all 3 criteria of testing.

The Results for Example 1 are as follows:

Transmittance of light at 700 nm=92%

Initial viscosity: 2640 cps 8 week viscosity: 2840 cps

Appearance: clear and viscous liquid.

What is claimed is:

1. An aqueous cleansing composition comprising:
   (a) from about 6% to about 20% of at least one nonionic surfactant that is an alkyl polyglucosides;
   (b) from about 3% to about 10% of at least one amphoteric surfactant that is a betaine;
   (c) from about 2% to about 8% of at least one anionic surfactant selected from the group consisting of alkyl sulfates, alkyl ether sulfates, acyl isethionates, acyl glycinates, acyl taurates, acyl amino acids, acyl sarcosinates, sulfosuccinates, sulfonates, wherein the alkyl and acyl groups of all these compounds comprise from 6 to 24 carbon atoms, and mixtures of the foregoing salts; and
   (d) from about 0.1% to about 5% of at least one cationic conditioning surfactant, cationic conditioning amine, or a mixture thereof;
   wherein the amount of nonionic surfactant (a) present in the final composition is greater than the amount of the amphoteric surfactant (b), and the ratio of nonionic surfactant (a) to anionic surfactant (c) is at least 1.9:1, by weight, based on the weight percent of each surfactant in the final composition.

2. The composition of claim 1 wherein the at least one nonionic surfactant (a) is present in the composition in an amount of from about 7% to about 10%, by weight, based on the total of weight of the composition.

3. The composition of claim 2 wherein the nonionic surfactant (a) is selected from lauryl glucoside, decyl glucoside, coco glucoside, and mixtures thereof.

4. The composition of claim 1 wherein the amphoteric surfactant (b) is present in the composition in an amount of from about 4% to about 8%, by weight, based on the total of weight of the composition.

5. The composition of claim 4 wherein the at least one amphoteric surfactant (b) is selected from coco betaine, cocoamidopropyl betaine, behenyl betaine, capryl/capramidopropyl betaine, lauryl betaine, and mixtures thereof.

6. The composition of claim 1 wherein the anionic surfactant (c) is present in the composition in an amount of from about 2.5% to about 5%, by weight, based on the total of weight of the composition.

7. The composition of claim 1 wherein the at least one anionic surfactant (c) is selected from sodium lauryl sulfate, sodium laureth sulfate, sodium cocoyl isethionate, sodium lauroyl methyl isethionate, sodium cocoyl glycinate, sodium cocoyl taurate, sodium methyl cocoyl taurate, sodium cocoyl glycinate, potassium cocoyl glycinate, disodium laurel sulfosuccinate, sodium lauryl sulfoacetate, sodium C14-16 olefin sulfonate, and mixtures thereof.

8. The composition of claim 1 wherein the at least one cationic conditioning surfactant and/or cationic conditioning amine (d) is selected from mono- and di-alkyl quaternary ammonium or diammonium salts, a dimethylamine derivative, and mixtures thereof.

9. The composition of claim 8 wherein the cationic conditioning surfactant and/or cationic conditioning amine (d) is present in the composition in an amount of from about 0.5% to about 3% by weight, based on the total of weight of the composition.

10. The composition of claim 9 wherein the cationic surfactant and/or cationic conditioning amine (d) is selected from behentrimonium chloride, cetrimonium chloride, behetrimonium methosulfate, stearamidipropyl dimethylamine, and mixtures thereof.

11. The composition of claim 10 further comprising one or more component selected from a pH adjusting agent, a preservative, an antioxidant, a fragrance, a chelating agent, a colorant, and mixtures thereof.

12. The composition of claim 1 having a viscosity from about 3000 cPs to about 6000 cPs.

13. The composition of claim 1 having a pH from about 4 to about 8.

14. An aqueous cleansing and conditioning composition comprising:
   (a) from about 6% to about 20% of at least one nonionic surfactant selected from lauryl glucoside, decyl glucoside, and mixtures thereof;
   (b) from about 3% to about 10% of cocoamidopropyl betaine;
   (c) from about 2% to about 8% of at least one anionic surfactant selected from sodium cocoyl glycinate, sodium cocoyl taurate, sodium laureth sulfate, sodium laureth sulfoscuccinate, sodium lauryl sulfoacetate, and mixtures thereof; and
   (d) from about 0.1% to about 5% of at least one cationic conditioning surfactant, cationic conditioning amine, or a mixture thereof;
   wherein the amount of nonionic surfactant (a) present in the final composition is greater than the amount of the amphoteric surfactant (b), and the ratio of nonionic surfactant (a) to anionic surfactant (c) is from about 1.9:1 to about 5:1, based on the weight percent of each surfactant in the final composition.

15. The composition of claim 14 wherein the cationic conditioning surfactant and/or cationic conditioning amine (d) is selected from behentrimonium chloride, cetrimonium chloride, behentrimonium methosulfate, stearyl dimethyl amine, stearamidopropyl dimethylamine, brassicamidopropyl dimethylamine, and mixtures thereof.

16. The composition of claim 15 wherein the cationic conditioning surfactant and/or cationic conditioning amine (d) is selected from stearamidipropyl dimethylamine, cetrimonium chloride, behentrimonium chloride, and mixtures thereof.

17. A method of cleansing and conditioning hair comprising contacting the hair with a composition according to claim 1.

18. A method of conditioning a keratinous substrate comprising contacting the keratinous substrate with the composition of claim 14.

19. A method of increasing the deposition of non-ionic silicone polymers onto a keratinous substrate comprising contacting the keratinous substrate with a non-ionic silicone polymer and the composition of claim 14.

20. A method of increasing the deposition of hydrophobic non-ionic conditioning agents onto a keratinous substrate comprising contacting the keratinous substrate with a non-ionic conditioning agent and the composition of claim 14.

21. The composition of claim 1, wherein the at least one anionic surfactant (c) is a sulfate.

22. The composition of claim 14, wherein the at least one anionic surfactant (c) is sodium laureth sulfate.

* * * * *